US011172878B2

(12) United States Patent
Bashan et al.

(10) Patent No.: US 11,172,878 B2
(45) Date of Patent: *Nov. 16, 2021

(54) APPARATUS AND SYSTEM FOR DIABETES MANAGEMENT

(71) Applicant: Hygieia, Inc., Ann Arbor, MI (US)

(72) Inventors: Eran Bashan, Ann Arbor, MI (US); Israel Hodish, Ann Arbor, MI (US)

(73) Assignee: HYGIEIA, INC., Livonia, MI (US)

( * ) Notice: Subject to any disclaimer, the term of this patent is extended or adjusted under 35 U.S.C. 154(b) by 895 days.

This patent is subject to a terminal disclaimer.

(21) Appl. No.: 15/878,050

(22) Filed: Jan. 23, 2018

(65) Prior Publication Data

US 2018/0146920 A1 May 31, 2018

Related U.S. Application Data

(63) Continuation of application No. 14/631,525, filed on Feb. 25, 2015, now Pat. No. 9,907,508, which is a
(Continued)

(51) Int. Cl.
*A61B 5/00* (2006.01)
*A61B 5/145* (2006.01)
(Continued)

(52) U.S. Cl.
CPC ........ *A61B 5/4839* (2013.01); *A61B 5/14532* (2013.01); *A61M 5/1684* (2013.01);
(Continued)

(58) Field of Classification Search
CPC .. A61B 5/4839; A61B 5/14532; G16H 20/60; G16H 20/17; G16H 20/10; G16H 10/40;
(Continued)

(56) References Cited

U.S. PATENT DOCUMENTS

| 4,403,984 A | 9/1983 | Ash et al. |
| 4,731,726 A | 3/1988 | Allen |

(Continued)

FOREIGN PATENT DOCUMENTS

| WO | 2003/065033 | 8/2003 |
| WO | 2005/072792 | 8/2005 |

(Continued)

OTHER PUBLICATIONS

Bu, Davis et al. "Benefits of Information Technology-Enabled Diabetes Management," *Diabetes Care*, 30:5 (May 2007) 1137-1142.
(Continued)

*Primary Examiner* — Amber R Stiles
(74) *Attorney, Agent, or Firm* — Jones Day (57) ABSTRACT

An apparatus and system diabetes management. The apparatus comprises a body which houses: (i) at least a first memory for storing data inputs corresponding at least to one or more components in a patient's present insulin dosage regimen and the patient's blood-glucose-level measurements determined at a plurality of times; (ii) a processor operatively connected to the at least first memory, the processor programmed at least to determine from the data inputs corresponding to the patient's blood-glucose-level measurements determined at a plurality of times whether and by how much to vary at least one of the one or more components of the patient's present insulin dosage regimen; (iii) a display screen operatively connected to the processor, (iv) a quantity of insulin; (v) a needle communicating with the quantity of insulin for delivering insulin to the patient; (vi) means for effecting delivery of a portion of the quantity of insulin to the patient via the needle; and (vii) metering means for controlling the portion of the quantity of insulin delivered to the patient via the needle.

8 Claims, 4 Drawing Sheets

Related U.S. Application Data continuation of application No. 13/128,358, filed as application No. PCT/US2009/063989 on Nov. 11, 2009, now Pat. No. 8,992,464.

(60) Provisional application No. 61/113,252, filed on Nov. 11, 2008, provisional application No. 61/257,886, filed on Nov. 4, 2009.

(51) Int. Cl.

| | |
|---|---|
| *G16H 40/63* | (2018.01) |
| *G16H 20/60* | (2018.01) |
| *A61M 5/168* | (2006.01) |
| *A61M 5/172* | (2006.01) |
| *G16H 20/17* | (2018.01) |
| *G16H 20/10* | (2018.01) |
| *G16H 10/40* | (2018.01) |
| *A61M 5/315* | (2006.01) |
| *A61M 5/142* | (2006.01) |

(52) U.S. Cl.
CPC .......... *A61M 5/1723* (2013.01); *G16H 10/40* (2018.01); *G16H 20/10* (2018.01); *G16H 20/17* (2018.01); *G16H 20/60* (2018.01); *G16H 40/63* (2018.01); *A61M 5/31571* (2013.01); *A61M 2005/14208* (2013.01); *A61M 2205/502* (2013.01); *A61M 2205/507* (2013.01); *A61M 2205/52* (2013.01)

(58) Field of Classification Search
CPC ... G16H 40/63; A61M 5/1684; A61M 5/1723; A61M 5/31571; A61M 2005/14208; A61M 2205/502; A61M 2205/507; A61M 2205/52
See application file for complete search history.

(56) References Cited

U.S. PATENT DOCUMENTS

| | | | |
|---|---|---|---|
| 4,981,779 A | 1/1991 | Wagner | |
| 5,216,597 A | 6/1993 | Beckers | |
| 5,251,126 A | 10/1993 | Kahn et al. | |
| 5,536,249 A * | 7/1996 | Castellano | G16H 20/17 |
| | | | 604/65 |
| 5,582,598 A | 12/1996 | Chanoch | |
| 5,822,715 A | 10/1998 | Worthington et al. | |
| 5,827,232 A | 10/1998 | Chanock et al. | |
| 5,840,020 A | 11/1998 | Heinonen et al. | |
| 5,956,501 A | 9/1999 | Brown | |
| 6,024,699 A | 2/2000 | Surwit et al. | |
| 6,186,145 B1 | 2/2001 | Brown | |
| 6,233,539 B1 | 5/2001 | Brown | |
| 6,379,301 B1 | 4/2002 | Worthington et al. | |
| 6,540,672 B1 | 4/2003 | Simonsen et al. | |
| 6,544,212 B2 | 4/2003 | Galley et al. | |
| 6,560,471 B1 | 5/2003 | Heller et al. | |
| 6,565,114 B1 | 5/2003 | Thomas | |
| 6,575,905 B2 | 6/2003 | Knobbe et al. | |
| 6,669,663 B1 | 12/2003 | Thompson | |
| 6,740,072 B2 | 5/2004 | Starkweather et al. | |
| 7,025,425 B2 | 4/2006 | Kovatchev et al. | |
| 7,039,560 B2 | 5/2006 | Kawatahara et al. | |
| 7,060,059 B2 | 6/2006 | Keith et al. | |
| 7,108,680 B2 | 9/2006 | Rohr et al. | |
| 7,137,951 B2 | 11/2006 | Pilarski | |
| 7,167,818 B2 | 1/2007 | Brown | |
| 7,204,823 B2 | 4/2007 | Estes et al. | |
| 7,267,665 B2 | 9/2007 | Steil et al. | |
| 7,282,029 B1 | 10/2007 | Poulsen et al. | |
| 7,291,107 B2 | 11/2007 | Hellwig et al. | |
| 7,404,796 B2 | 7/2008 | Ginsberg | |
| 7,509,156 B2 | 3/2009 | Flanders | |
| 7,553,281 B2 | 6/2009 | Hellwig et al. | |
| 7,651,845 B2 | 1/2010 | Doyle et al. | |
| 7,734,323 B2 | 6/2010 | Blomquist | |
| 7,853,455 B2 | 12/2010 | Brown | |
| 7,877,271 B2 | 1/2011 | Brown | |
| 7,901,625 B2 | 3/2011 | Brown | |
| 7,904,310 B2 | 3/2011 | Brown | |
| 7,912,688 B2 | 3/2011 | Brown | |
| 7,920,998 B2 | 4/2011 | Brown | |
| 7,949,507 B2 | 5/2011 | Brown | |
| 8,992,464 B2 * | 3/2015 | Bashan | G16H 20/17 |
| | | | 604/66 |
| 9,907,508 B2 * | 3/2018 | Bashan | G16H 20/10 |
| 2003/0028089 A1 | 2/2003 | Galley et al. | |
| 2003/0050621 A1 | 3/2003 | Lebel et al. | |
| 2004/0042272 A1 | 3/2004 | Kurata | |
| 2004/0054263 A1 | 3/2004 | Moerman et al. | |
| 2004/0044272 A1 | 4/2004 | Moerman et al. | |
| 2005/0049179 A1 | 3/2005 | Davidson et al. | |
| 2005/0055010 A1 | 3/2005 | Pettis et al. | |
| 2005/0165363 A1 * | 7/2005 | Judson | A61M 5/31551 |
| | | | 604/209 |
| 2005/0171503 A1 | 8/2005 | Berghe et al. | |
| 2005/0177398 A1 | 8/2005 | Watanabe et al. | |
| 2005/0192494 A1 * | 9/2005 | Ginsberg | G16H 20/17 |
| | | | 600/365 |
| 2005/0192557 A1 | 9/2005 | Brauker et al. | |
| 2005/0197533 A1 | 9/2005 | May et al. | |
| 2005/0197621 A1 | 9/2005 | Poulsen et al. | |
| 2005/0272640 A1 | 12/2005 | Doyle et al. | |
| 2006/0160722 A1 | 7/2006 | Green et al. | |
| 2006/0173260 A1 | 8/2006 | Gaoni et al. | |
| 2006/0173417 A1 * | 8/2006 | Rosen | A61M 5/14244 |
| | | | 604/187 |
| 2006/0224109 A1 | 10/2006 | Steil et al. | |
| 2006/0264886 A9 | 11/2006 | Pettis et al. | |
| 2007/0078314 A1 | 4/2007 | Grounsell et al. | |
| 2007/0078818 A1 | 4/2007 | Zivitz et al. | |
| 2007/0168224 A1 | 7/2007 | Letzt et al. | |
| 2007/0293742 A1 | 12/2007 | Simonsen et al. | |
| 2008/0077072 A1 | 3/2008 | Keenan et al. | |
| 2008/0097289 A1 | 4/2008 | Steil et al. | |
| 2008/0119705 A1 | 5/2008 | Patel et al. | |
| 2008/0139907 A1 | 6/2008 | Roa | |
| 2008/0172030 A1 | 7/2008 | Blomquist | |
| 2008/0214919 A1 | 9/2008 | Harmon et al. | |
| 2008/0234943 A1 | 9/2008 | Ray et al. | |
| 2008/0269585 A1 | 10/2008 | Ginsberg | |
| 2009/0069636 A1 | 3/2009 | Zivitz et al. | |
| 2009/0088690 A1 | 4/2009 | Carter et al. | |
| 2009/0247982 A1 | 10/2009 | Krulevitch et al. | |
| 2009/0253970 A1 | 10/2009 | Bashan | |
| 2009/0253973 A1 | 10/2009 | Bashan | |
| 2009/0299152 A1 | 12/2009 | Taub et al. | |
| 2010/0016700 A1 | 1/2010 | Sieh et al. | |
| 2010/0124996 A1 | 5/2010 | Lindsay | |
| 2010/0160740 A1 | 6/2010 | Cohen et al. | |
| 2010/0161236 A1 | 6/2010 | Cohen et al. | |
| 2010/0161346 A1 | 6/2010 | Getschmann et al. | |
| 2010/0256047 A1 | 10/2010 | Sieh et al. | |
| 2010/0305545 A1 | 12/2010 | Kanderian et al. | |
| 2010/0331652 A1 | 12/2010 | Groll et al. | |
| 2010/0331654 A1 | 12/2010 | Jerdonek et al. | |

FOREIGN PATENT DOCUMENTS

| | | |
|---|---|---|
| WO | 2005/110222 | 11/2005 |
| WO | 2007/116226 | 10/2007 |
| WO | 2009/146119 | 12/2009 |
| WO | 2009/146121 | 12/2009 |
| WO | 2010/056718 | 5/2010 |
| WO | 2010/075350 | 7/2010 |
| WO | 2010/089304 | 8/2010 |
| WO | 2010/089305 | 8/2010 |

(56) References Cited

FOREIGN PATENT DOCUMENTS

| | | |
|---|---|---|
| WO | 2010/089306 | 8/2010 |
| WO | 2010/089307 | 8/2010 |

OTHER PUBLICATIONS

Hayes, R. P. et al. "Primary Care Physician Beliefs About Insulin Initiation in Patients with Type 2 Diabetes," *Int J Clin Pract*, 62:6 (Jun. 2008) 860-868.

Bretzel, Reinhard G et al. "Once-Daily Basal Insulin Glargine Versus Thrice-Daily Prandial Insulin Lispro in People with Type 2 Diabetes on Oral Hypoglycaemic Agents (APOLLO): An Open Randomised Controlled Trial," *Lancet*, 371 (2008) 1073-1084.

Bergenstal, Richard M. et al. "Adjust to Target in Type 2 Diabetes: Comparison of a Simple Algorithm with Carbohydrate Counting for Adjustment of Mealtime Insulin Glulisine," *Diabetes Care*, 31:7 (Jul. 2008) 1305-1310.

Deutsch, T et al. "UTOPIA: A Consultation System for Visit-by-Visit Diabetes Management," *Med Inform*, 21:4 (1996) 345-358.

Albisser, A. M. "Devices for the Control of Diabetes Mellitus," *Proceedings of the IEEE*, 67:9 (Sep. 1979) 1308-1320.

Deutsch, T. et al., "Computer-Assisted Diabetic Management: A Complex Approach," *Computer Methods and Programs in BioMedicine*, 32 (1990) 195-214.

Farmer, Terry G., Jr, et al. "The Future of Open- and Closed-Loop Insulin Delivery Systems," *Journal of Pharmacy and Pharmacology*, 60 (2008) 1-13.

Cramer, J. A. et al. "The Significance of Compliance and Persistence in the Treatment of Diabetes, Hypertension and Dyslipidaemia: A Review," *Int J Clin Pract*, 62:1 (Jan. 2008) 76-87.

American Diabetes Association Statement, "Economic Costs of Diabetes in the U.S. in 2007," *Diabetes Care*, 31:3 (Mar. 2008) 596-615.

Andreassen, Steen et al. "A Probabilistic Approach to Glucose Prediction and Insulin Dose Adjustment: Description of Metabolic Model and Pilo Evaluation Study," *Computer Methods and Programs in BioMedicine*, 41 (1994) 153-165.

Day, J. P. "Some Considerations of Legal Liability Concerning the Use and Future Development of Knowledge Based or Expert Systems in Diabetes Care," *Diab Nutr Metab*, 8:4 (1995) 195-200.

Chiarelli, Francesco et al. "Controlled Study in Diabetic Children Comparing Insulin-Dosage Adjustment by Manual and Computer Algorithms," *Diabetes Care*, 13:10 (Oct. 1990) 1080-1088.

Nathan, David M. et al. "Translating the A1C Assay into Estimated Average Glucose Values," *Diabetes Care*, 31:8 (Aug. 2008) 1-6.

Deutsch, T. et al. "Time Series Analysis and Control of Blood Glucose Levels in Diabetic Patients," *Computer Methods and Programs in BioMedicine*, 41 (1994) 167-182.

Ray, Kausik K. et al. "Effect of Intensive Control of Glucose on Cardiovascular Outcomes and Death in Patients with Diabetes Mellitus: a Meta-Analysis of Randomized Controlled Trials," *Lancet*, 373 (May 23, 2009) 1765-1772.

Ryff-de Lèche, Arnika et al. "Clinical Application of Two Computerized Diabetes Management Systems; Comparison with the Log-Book Method," *Diabetes Research*, 19(1992) 97-105.

Janka, Hans U. et al. "Comparison of Basal Insulin Added to Oral Agents Versus Twice-Daily Premixed Insulin as Initial Insulin Therapy for Type 2 Diabetes," *Diabetes Care*, 28:2 (Feb. 2005) 254-259.

Lougheed, W. D. et al. "Stabilizing Blood Glucose with a Novel Medical Expert System," *Biosensors*, 3(1988) 381-389.

Pernick, Nat L. et al. "Personal Computer Programs to Assist with Self-Monitoring of Blood Glucose and Self-Adjustment of Insulin Dosage," *Diabetes Care*, 9:1 (Jan.-Feb. 1986) 61-69.

Spoelstra, José A. et al. "Refill Compliance in Type 2 Diabetes Mellitus: A Predictor of Switching to Insulin Therapy?" *Pharmacoepidemiology and Drug Safety*, 12 (2003) 121-127.

Marshall, Trevor G. et al. "New Microprocessor-Based Insulin Controller," *IEEE Transactions on BioMedical Engineering*, BME-30:11 (Nov. 1983) 689-695.

Barnett, Anthony "Dosing of Insulin Glargine in the Treatment of Type 2 Diabetes," *Clinical Therapeutics*, 29:6 (Jun. 2007) 987-999.

Herman, William H. et al. "A Clinical Trial of Continuous Subcutaneous Insulin Infusion Versus Multiple Daily Injections in Older Adults with Type 2 Diabetes," *Diabetes Care*, 28:7 (Jul. 2005) 1568-1573.

Eliaschewitz, Freddy G. et al. "Therapy in Type 2 Diabetes: Insulin Glargine vs. NPH Insulin Both in Combination with Glimepiride," *Archives of Medical Research*, 37 (2006) 495-501.

Hoerger, Thomas J et al. "Is Glycemic Control Improving in U.S. Adults?" *Diabetes Care*, 31:1 (Jan. 2008) 81-86.

Albisser, A. M. "The Role(s) of Glucose Sensing in Diabetes: Informative, Archival, or Control?" *Annual International Conference of the IEEE Engineering in Medicine and Biology Society*, 12:2 (1990) 0474-0475.

Nathan, David M. et al. "Medical Management of Hyperglycemia in Type 2 Diabetes: A Consensus Algorithm for the Initiation and Adjustment of Therapy," *Diabetes Care*, 31:12 (Dec. 2008) 1-11.

Albisser, A. Michael "Intelligent Instrumentation in Diabetic Management," *Critical Reviews in BioMedical Engineering*, 17:1 (1989) 1-24.

Miyako, Kenichi et al. "Improved Diabetes Control by Using 'Close Adjustment Algorithms'," *Pediatrics International*, 46 (2004) 678-684.

Lehmann, E. D. "Application of Computers in Clinical Diabetes Care," *Diab Nutr Metab*, 10 (1997) 45-59.

Hirsch, Irl B. et al. "Clinical Application of Emerging Sensor Technologies in Diabetes Management: Consensus Guidelines for Continuous Glucose Monitoring (CGM)," *Diabetes Technology & Therapeutics*, 10:4 (2008) 232-244.

Choe, Hae Mi et al. "Proactive Case Management of High-Risk Patients with Type 2 Diabetes Mellitus by a Clinical Pharmacist: A Randomized Controlled Trial," *Am J Manag Care*, 11:4 (2005) 253-260.

Schrezenmeir, J. et al. "Computer Assisted Insulin Dosage Adjustment—Perspectives for Diabetes Control," 1990.

Spellman, Craig W. "Management of Diabetes in the Real World: Tight Control of Glucose Metabolism," *JAOA*, Supplement 5, 103:8 (Aug. 2003) S8-S13.

Schiffrin, Alicia et al. "Computer-Assisted Insulin Dosage Adjustment," *Diabetes Care*, 8:6 (Nov./Dec. 1985) 545-552.

Albisser, A. M. et al. "Insulin Dosage Adjustment Using Manual Methods and Computer Algorithms: A Comparative Study," *Medical and Biological Engineering & Computing*, 24 (Nov. 1986) 577-584.

Hirsch, Irl B et al. "A Real-World Approach to Insulin Therapy in Primary Care Practice," *Clinical Diabetes*, 23:2 (2005) 78-86.

Lehmann, E. D. et al. "Compartmental Models for Glycaemic Prediction and Decision-Support in Clinical Diabetes Care: Promise and Reality," *Computer Methods and Programs in BioMedicine*, 56 (1998) 193-204.

Guler, Serdar et al. "Intensification Lessons with Modern Premixes: From Clinical Trial to Clinical Practice," *Diabetes Research and Clinical Practice*, 81S (2008) S23-S30.

Lehmann, E. D. et al. "Insulin Dosage Adjustment in Diabetes," *J Biomed Eng*, 14 (May 1992) 243-249.

Davies, M. et al. "Initiation of Insulin Glargine in Suboptimally Controlled Patients with Type 2 Diabetes: Sub-Analysis of the AT.LANTUS Trial Comparing Treatment Outcomes in Subjects From Primary and Secondary Care in the UK," *Diabetes, Obesity and Metabolism*, 9 (2007) 706-713.

Albisser, A. Michael "Six Generations of the Insulin Dosage Computer: A New Clinical Device for Diabetes Self-Management Through Specialized Centres," *Annual International Conference of the IEEE Engineering in Medicine and Biology Society*, 12:3 (1990) 0996-0997.

Davies, Melanie et al. "Improvement of Glycemic Control in Subjects with Poorly Controlled Type 2 Diabetes," *Diabetes Care*, 28:6 (Jun. 2005) 1282-1288.

(56) References Cited

OTHER PUBLICATIONS

Gomis, Ramon et al. "Improving Metabolic Control in Sub-Optimally Controlled Subjects with Type 1 Diabetes: Comparison of Two Treatment Algorithms Using Insulin Glargine," *Diabetes Research and Clinical Practice*, 77 (2007) 84-91.

Saaddine, Jinan B. et al. "Improvements in Diabetes Processes of Care and Intermediate Outcomes: United States, 1988-2002," *Annals of Internal Medicine*, 144 (2006) 465-474.

Van Herpe, Tom et al. "Glycemic Penalty Index for Adequately Assessing and Comparing Different Blood Glucose Control Algorithms," *Critical Care*, 12:1 (R24)(2008) 1-14.

Kennedy, Laurence et al. "Impact of Active Versus Usual Algorithmic Titration of Basal Insulin and Point-of-Care Versus Laboratory Measuremenet of HbA1c on Glycemic Control in Patients with Type 2 Diabetes," *Diabetes Care*, 29:1 (Jan. 2006) 1-8.

Brahams, Diana et al. "Decision Aids and the Law," *The Lancet* (Sep. 9, 1989) 632-634.

Meneghini, L. et al. "The Usage of a Simplified Self-Titration Dosing Guideline (303 Algorithm) for Insulin Detemir in Patients with Type 2 Diabetes—Results of the Randomized, Controlled PREDICTIVE™ 303 Study," *Diabetes, Obesity and Metabolism*, 9 (2007) 902-913.

Stratton, Irene M. et al. "Association of Glycaemia with Macrovascular and Microvascular Complications of Type 2 Diabetes (UKPDS 35): Prospective Observational Study," *BMJ*, 321 (Aug. 12, 2000) 405-412.

Dinsmoor, Robert S. "The Artificial Pancreas: How to 'Close the Loop'," *JDRF Countdown* (Winter 2007) 24-25.

Ford, Earl S. et al. "Trends in A1C Concentrations Among U.S. Adults with Diagnosed Diabetes From 1999 to 2004," *Diabetes Care*, 31:1 (Jan. 2008) 102-104.

Skyler, Jay S. et al. "Algorithms for Adjustment of Insulin Dosage by Patients Who Monitor Blood Glucose," Diabetes Care, 4:2 (Mar.-Apr. 1981) 311-318.

Lehmann, E. D. et al. "Application of Computers in Diabetes Care—A Review, I. Computers for Data Collection and Interpretation," *Med Inform*, 20:4 (1995) 281-302.

Lehmann, E. D et al. "Application of Computers in Diabetes Care—A Review, II. Computers for Decision Support and Education," *Med Inform*, 20:4 (1995) 303-329.

Davies, M. et al. "Initiation of Insulin Glargine Therapy in Type 2 Diabetes Subjects Suboptimally Controlled on Oral Antidiabetic Agents: Results from the AT.LANTUS Trial," *Diabetes, Obesity and Metabolism*, 10 (2008) 387-399.

Meneghini, Luigi et al. "An Electronic Case Manager for Diabetes Control," Diabetes Care, 21:4 (Apr. 1998) 591-596.

Buse, John B. et al. "DURAbility of Basal Versus Lispro Mix 75/25 Insulin Efficacy (DURABLE) Trial 24-Week Results," *Diabetes Care*, 32:6 (Jun. 2009) 1007-1013.

Balas, E. Andrew et al. "Computerized Knowledge Management in Diabetes Care," *Medical Care*, 42:6 (Jun. 2004) 610-621.

Berger, M. et al. "Computer Programs to Assist the Physician in the Analysis of Self-Monitored Blood Glucose Data," Nov. 1988, 52-57.

Raskin, Philip R. et al. "Basal Insulin or Premix Analogue Therapy in Type 2 Diabetes Patients," *European Journal of Internal Medicine*, 18 (2007) 56-62.

Koro, Carol E et al. "Glycemic Control From 1988 to 2000 Among U.S. Adults Diagnosed with Type 2 Diabetes," *Diabetes Care*, 27:1 (Jan. 2004) 17-20.

Mayfield, Jennifer A. et al. "Insulin Therapy for Type 2 Diabetes: Rescue, Augmentation, and Replacement of Beta-Cell Function," *American Family Physician*, 70:3 (Aug. 1, 2004) 489-500.

Peterson, Charles M. et al. "Randomized Trial of Computer-Assisted Insulin Delivery in Patients with Type I Diabetes Beginning Pump Therapy," *Am J Med*, 81 (Jul. 1986) 69-72.

Queale, William S. et al. "Glycemic Control and Sliding Scale Insulin Use in Medical in patients with Diabetes Mellitus," *Arch Intern Med*, 157 (Mar. 10, 1997) 545-552.

Holman, Rury R. et al. "Addition of Biphasic, Prandial, or Basal Insulin to Oral Therapy in Type 2 Diabetes," *N Engl J Med*, 357:17 (Oct. 25, 2007) 1716-1730.

Woodcock, Alison et al. "Patient Concerns in Their First Year with Type 2 Diabetes: Patient and Practice Nurse Views," *Patient Education and Counseling*, 42 (2001) 257-270.

Hermányi, István et al. "Management of Diabetes with the Use of a Microprocessor: Comparison of Insulin Treatments Based on Blood and Urine Glucose Levels," 1988, 33-40.

Farmer, Andrew J et al. "A Randomized Controlled Trial of the Effect of Real-Time Telemedicine Support on Glycemic Control in Young Adults with Type 1 Diabetes (ISRCTN 46889446)," *Diabetes Care*, 28:11 (Nov. 2005) 2697-2702.

Schulz, G. et al. "Diabetes Self-Adjustment by a Computerized Program—First Experiences in Inpatient and Outpatient Treatment," 1985, 578-582.

Ambrosiadou, B. V. et al. "Clinical Evaluation of the DIABETES Expert System for Decision Support by Multiple Regimen Insulin Dose Adjustment," *Computer Methods and Programs in BioMedicine*, 49 (1996) 105-115.

Hirsch, Irl B et al. "Self-Monitoring of Blood Glucose (SMBG) in Insulin- and Non-Insulin-Using Adults with Diabetes: Consensus Recommendations for Improving SMBG Accuracy, Utilization and Research," *Diabetes Technology & Therapeutics*, 10:6 (2008) 419-440.

Buse et al., "The Durable Trial, 24-Week esults.", Jun. 2009.

Nathan, David M. et al. "Management of Hyperglycemia in Type 2 Diabetes: A Consensus Algorithm for the Initiation and Adjustment of Therapy," *Diabetes Care*, 29:8 (Aug. 2006) 1963-1972.

Aubert, Ronald E et al. "Nurse Case Management to Improve Glycemic Control in Diabetic Patients in a Health Maintenance Organization," 129:8 (Oct. 15, 1998) 605-612.

Lehmann, E. D. et al. "Retrospective Validation of a Physiological Model of Glucose-Insulin Interaction in Type 1 Diabetes Mellitus," *Med Eng Phys*, 16 (May 1994) 193-202.

Albisser, A. Michael "Toward Algorithms in Diabetes Self-Management," *Diabetes Technology & Therapeutics*, 5:3 (2003) 371-373.

Albisser, A. M. et al. "Electronics and the Diabetic," *IEEE Transactions on Biomedical Engineering*, BME-29:4 (Apr. 1982) 239-248.

European Diabetes Policy Group 1998 "Desktop Guide to Type 1 (Insulin-Dependent) Diabetes Mellitus," *Diabetic Medicine*, 16 (1999) 253-266.

European Diabetes Policy Group 1999 "Desktop Guide to Type 2 Diabetes Mellitus," *Diabetic Medicine*, 16 (1999) 716-730.

Action to Control Cardiovascular Risk in Diabetes (ACCORD) Trial—*Protocol*, May 11, 2005, 1-167.

Jenkins, Alicia J. et al. "Evaluation of an Algorithm to Guide Patients with Type 1 Diabetes Treated with Continuous Subcutaneous Insulin Infusion on How to Respond to Real-Time Continuous Glucose Levels," *Diabetes Care*, 33:6 (Jun. 2010) 1242-1248.

Charpentier, Guillaume et al. "The Diabeo Software Enabling Individualized Insulin Dose Adjustments Combined with Telemedicine Support Improves $HbA_{1c}$ in Poorly Controlled Type 1 Diabetic Patients," *Diabetes Care* (online: care.diabetesjournals.org)(Jan. 25, 2011) 1-7.

Mulvaney, Shelagh A. et al. "An Internet-Based Program to Improve Self-Management in Adolescents with Type 1 Diabetes," *Diabetes Care*, 33:3 (Mar. 2010) 602-604.

Strange, Poul "Treat-to-Target Insulin Titration Algorithms When Initiating Long or Intermediate Acting Insulin in Type 2 Diabetes," *Journal of Diabetes Science and Technology*, 1:4 (Jul. 2007) 540-548.

The Juvenile Diabetes Research Foundation Continuous Glucose Monitoring Study Group "Continuous Glucose Monitoring and Intensive Treatment of Type 1 Diabetes," *N Eng J Med*, 359 (2008) 1-13.

(56) References Cited

OTHER PUBLICATIONS

Renard, Eric "Clinical Experience with an Implanted Closed-Loop Insulin Delivery System," *Arq Bras Endrocrinol Metab*, 52:2 (2008) 349-354 (with English Abstract).

Oyer, David S. "$A_{1c}$ Control in a Primary Care Setting: Self-Titrating an Insulin Analog Pre-Mix (INITIATE*plus* Trial)," *Am J Med*, 122:11 (Nov. 2009) 1043-1049.

Stone, Roslyn A. et al. "Active Care Management Supported by Home Telemonitoring in Veterans with Type 2 Diabetes," *Diabetes Care*, 33:3 (Mar. 2010) 478-484.

Quinn, Charlene C et al. "Cluster-Randomized Trial of a Mobile Phone Personalized Behavioral Intervention for Blood Glucose Control," *Diabetes Care* (online: care.diabetesjournals.org)(Jul. 25, 2011) 1-9.

Bergenstal, Richard M. et al. "Effectiveness of Sensor-Augmented Insulin-Pump Therapy in Type 1 Diabetes," *N Eng J Med*, 363:4 (Jul. 22, 2010) 311-320.

Miller, Shahar et al. "Automatic Learning Algorithm for the MD-Logic Artificial Pancreas System," *Diabetes Technology & Therapeutics*, 13:10 (2011) 1-8.

Kilbride, Lynn et al. "Managing Blood Glucose During and After Exercise in Type 1 Diabetes: Reproducibility of Glucose Response and a Trial of a Structured Algorithm Adjusting Insulin and Carbohydrate Intake," *Journal of Clinical Nursing* (2011) 1-7.

Campos-Cornejo, Fabiola et al. "An Advisory Protocol for Rapid- and Slow-Acting Insulin Therapy Based on a Run-to-Run Methodology," *Diabetes Technology & Therapeutics*, 12:7 (2010) 555-565.

International Search Report for PCT/US2009/039418 dated Nov. 17, 2009.

International Search Report for PCT/US2009/063989 dated May 28, 2010.

International Search Report for PCT/US2010/055246 dated Dec. 13, 2010.

International Search Report for PCT/US2009/039421 dated Nov. 17, 2009.

\* cited by examiner

APPARATUS AND SYSTEM FOR DIABETES MANAGEMENT

CROSS-REFERENCE TO RELATED APPLICATIONS

This application is a continuation of U.S. application Ser. No. 14/631,525, filed Feb. 25, 2015, which is continuation of U.S. application Ser. No. 13/128,358, filed Jul. 21, 2011, now U.S. Pat. No. 8,992,464, which is the National Phase application of International Application No. PCT/AU2009/063989, filed 11 Nov. 2009, which designates the United States and was published in English, which claims priority to U.S. provisional application No. 61/113,252, filed 11 Nov. 2008, and U.S. provisional application No. 61/257,886, filed 4 Nov. 2009. Each of these applications, in their entirety, are incorporated herein by reference.

FIELD OF THE INVENTION

The present invention pertains to apparatus and systems for diabetes management, and more specifically to such apparatus and systems as are operative to determined at a plurality of times whether and by how much to vary at least one of the one or more components of a patient's present insulin dosage regimen, and to provide the means for administering insulin doses.

BACKGROUND

Diabetes is a chronic disease resulting from deficient insulin secretion by the endocrine pancreas. About 7% of the general population in the Western Hemisphere suffers from diabetes. Of these persons, roughly 90% suffer from Type-2 diabetes while approximately 10% suffer from Type-1. In Type-1 diabetes, patients effectively surrender their endocrine pancreas to autoimmune distraction and so become dependent on daily insulin injections to control blood-glucose-levels. In Type-2 diabetes, on the other hand, the endocrine pancreas gradually fails to satisfy increased insulin demands, thus requiring the patient to compensate with a regime of oral medications or insulin therapy. In the case of either Type-1 or Type-2 diabetes, the failure to properly control glucose levels in the patient may lead to such complications as heart attacks, strokes, blindness, renal failure, and even premature death.

Insulin therapy is the mainstay of Type-1 diabetes management and one of the most widespread treatments in Type-2 diabetes, about 27% of the sufferers of which require insulin. Insulin administration is designed to imitate physiological insulin secretion by introducing two classes of insulin into the patient's body: Long-acting insulin, which fulfills basal metabolic needs; and short-acting insulin (also known as fast-acting insulin), which compensates for sharp elevations in blood-glucose-levels following patient meals. Orchestrating the process of dosing these two types of insulin, in whatever form (e.g., separately or as premixed insulin) involves numerous considerations.

First, patients measure their blood-glucose-levels (using some form of a glucose meter) on average about 3 to 4 times per day. The number of such measurements and the variations therebetween complicates the interpretation of these data, making it difficult to extrapolate trends therefrom that may be employed to better maintain the disease. Second, the complexity of human physiology continuously imposes changes in insulin needs for which frequent insulin dosage regimen adjustments are warranted. Presently, these considerations are handled by a patient's endocrinologist or other healthcare professional during clinic appointments. Unfortunately, these visits are relatively infrequent—occurring once every 3 to 6 months—and of short duration, so that the physician or other healthcare professional is typically only able to review the very latest patient medical data. In consequence, it has been shown that more than 60% of patients control their diabetes at sub-optimal levels, leading to unwanted complications from the disease.

Indeed, one of the major obstacles of diabetes management is the lack of availability of a patient's healthcare professional and the relative infrequency of clinic appointments. Studies have, in fact, established that more frequent insulin dosage regimen adjustments—e.g., every 1 to 2 weeks—improves diabetes control in most patients. Yet as the number of diabetes sufferers continues to expand, it is expected that the possibility of more frequent insulin dosage regimen adjustments via increased clinic visits will, in fact, decrease. And, unfortunately, conventional diabetes treatment solutions do not address this obstacle.

The device most commonly employed in diabetes management is the blood glucose meter. Such devices come in a variety of forms, although all are characterized by their ability to provide patients near instantaneous readings of their blood-glucose-levels. This additional information can be used to better identify dynamic trends in blood-glucose-levels. However, all conventional glucose meters are designed to be diagnostic tools rather than therapeutic ones. Therefore, by themselves, even state-of-the-art glucose meters do not lead to improved glycemic control.

One conventional solution to the treatment of diabetes is the insulin pump. Insulin pumps are devices that continuously infuse short acting insulin into a patient at a predetermined rate to cover both basal needs and meals. As with manual insulin administration therapy, a healthcare professional sets the pump with the patient's insulin dosage regimen during clinic visits. In addition to their considerable current expense, which prohibits their widespread use by patients with Type-2 diabetes, insulin pumps require frequent adjustment by the physician or other healthcare professional to compensate for the needs of individual patients based upon frequent blood-glucose-level measurements.

An even more recent solution to diabetes treatment seeks to combine an insulin pump and near-continuous glucose monitoring in an effort to create, in effect, an artificial pancreas regulating a patient's blood-glucose-level with infusions of short-acting insulin. According to this solution, real-time patient information is employed to match insulin dosing to the patient's dynamic insulin needs irrespective of any underlying physician-prescribed treatment plan. While such systems address present dosing requirements, they are entirely reactive and not instantaneously effective. In consequence of these drawbacks, such combined systems are not always effective at controlling blood glucose levels. For instance, such combined units cannot forecast unplanned activities, such as exercise, that may excessively lower a patient's blood-glucose level. And when the hypoglycemic condition is detected, the delay in the effectiveness of the insulin occasioned not only by the nature of conventional synthetic insulin but also the sub-dermal delivery of that insulin by conventional pumps results in inefficient correction of the hypoglycemic event.

While the foregoing solutions are beneficial in the management and even treatment of diabetes in some patients, or at least hold the promise of being so, there continues to exist the need for an apparatus that is easy to use so as to facilitate improved diabetes control in patients.

SUMMARY

The present invention comprehends an apparatus and system for diabetes management. In one embodiment, the inventive apparatus comprises a body which houses:
  (i) at least a first memory for storing data inputs corresponding at least to one or more components in a patient's present insulin dosage regimen and the patient's blood-glucose-level measurements determined at a plurality of times;
  (ii) a processor operatively connected to the at least first memory, the processor programmed at least to determine from the data inputs corresponding to the patient's blood-glucose-level measurements determined at a plurality of times whether and by how much to vary at least one of the one or more components of the patient's present insulin dosage regimen;
  (iii) a display screen operatively connected to the processor and operative to display at least the recommended insulin dose;
  (iv) a quantity of insulin;
  (v) a needle communicating with the quantity of insulin for delivering insulin to the patient;
  (vi) means for effecting delivery of a portion of the quantity of insulin to the patient via the needle; and
  (vii) metering means for controlling the portion of the quantity of insulin delivered to the patient via the needle.

In one embodiment, the apparatus may be for single-use only, meaning that the quantity of insulin cannot be replenished upon exhaustion thereof.

In another embodiment, the apparatus is for multiple-use and the quantity of insulin is therefore able to be replenished. According to this embodiment, the quantity of insulin may be contained in a cartridge that is selectively removable from the housing so as to be replaceable upon exhaustion of the quantity of insulin therein.

In one embodiment, the body may further house a test strip port for receiving a test strip. Per this embodiment, the processor is operative to determine a patient's current blood glucose level measurement from a sample of the patient's blood provided on a test strip. Also per this embodiment, the display may, optionally, be operative to display a patient's current blood glucose level measurement.

According to one feature of the invention, means may be provided for communicating data from the memory to a remote device for remote storage. Such means are particularly, though not exclusively, suited to employment of the apparatus for single-use only, according to which data stored in the apparatus may be remotely stored, including, for example, for later transfer to a second, like apparatus.

Per another feature, means may be provided communicating data from the memory of the apparatus directly to a second, like apparatus for diabetes management. Such means are particularly, though not exclusively, suited to employment of the apparatus for single-use only.

Per yet another feature of the invention, the apparatus may further comprise means for preventing a patient from administering an injection when there is an insufficient quantity of insulin remaining in the apparatus.

The present invention further comprehends a system for diabetes management, comprising:
  (a) a device including:
    (i) at least a first memory for storing data inputs corresponding at least to one or more components in a patient's present insulin dosage regimen and the patient's blood-glucose-level measurements determined at a plurality of times; and
    (ii) a processor operatively connected to the at least first memory, the processor programmed at least to determine from the data inputs corresponding to the patient's blood-glucose-level measurements determined at a plurality of times whether and by how much to vary at least one of the one or more components of the patient's present insulin dosage regimen;
  (b) an apparatus, remote from the device, comprising a body housing:
    (i) at least a first memory;
    (ii) a processor operatively connected to the at least first memory;
    (iii) a display screen operatively connected to the processor;
    (iv) a quantity of insulin;
    (v) a needle communicating with the quantity of insulin for delivering insulin to a patient;
    (vi) means for effecting delivery of a portion of the quantity of insulin to the patient via the needle; and
    (vii) metering means for controlling the portion of the quantity of insulin delivered to the patient via the needle; and
  (c) means for communicating data between the device and the apparatus, the data including at least data corresponding to a current recommended insulin dose.

In one embodiment, the apparatus may be for single-use only. Accordingly, the quantity of insulin cannot be replenished.

In another embodiment, the apparatus is for multiple-use and the quantity of insulin is therefore able to be replenished. According to this embodiment, the quantity of insulin may be contained in a cartridge that is selectively removable from the housing so as to be replaceable upon exhaustion of the quantity of insulin therein.

According to one feature of the invention, the body further houses a test strip port for receiving a test strip, and the processor of the apparatus is operative to determine the patient's current blood glucose level measurement from a sample of the patient's blood provided on a test strip, and wherein further the means for communicating between the device and the apparatus are further operative for communicating the patient's blood glucose measurement between the apparatus and the device.

Per yet another feature of the invention, the apparatus may further comprise means for preventing a patient from administering an injection when there is an insufficient quantity of insulin remaining in the apparatus.

BRIEF DESCRIPTION OF THE DRAWINGS

For a better understanding of the invention, and to show more clearly how it may be carried into effect according to one or more embodiments thereof, reference will now be made, by way of example, to the accompanying drawings, showing exemplary embodiments of the present invention and in which.

WRITTEN DESCRIPTION

As required, detailed embodiments of the present invention are disclosed herein. However, it is to be understood that the disclosed embodiment is merely exemplary of the invention that may be embodied in various and alternative forms. Therefore, specific structural and functional details disclosed herein are not to be interpreted as limiting, but merely as a representative basis for teaching one skilled in the art to variously employ the present invention.

The accompanying drawings are not necessarily to scale, and some features may be exaggerated or minimized to show details of particular components or elements.

As used herein, the term "insulin dose" means and refers to the quantity of insulin taken on any single occasion, while the term "insulin dosage regimen" refers to and means the set of instructions (typically defined by the patient's physician or other healthcare professional) defining when and how much insulin to take in a given period of time and/or under certain conditions. One conventional insulin dosage regimen comprises several components, including a long-acting insulin dosage component, a plasma glucose correction factor component, and a carbohydrate ratio component. Thus, for instance, an exemplary insulin dosage regimen for a patient might be as follows: 25 units of long acting insulin at bedtime; 1 unit of fast-acting insulin for every 10 grams of ingested carbohydrates; and 1 unit of fast-acting insulin for every 20 mg/dL by which a patient's blood glucose reading exceeds 120 mg/dL. In the context of this disclosure, a "current" insulin dose equates to the number of insulin units the patient needs to administer on the basis of the latest blood-glucose-level measurement and his or her prevailing insulin dosage regimen.

Figures 1, 2:
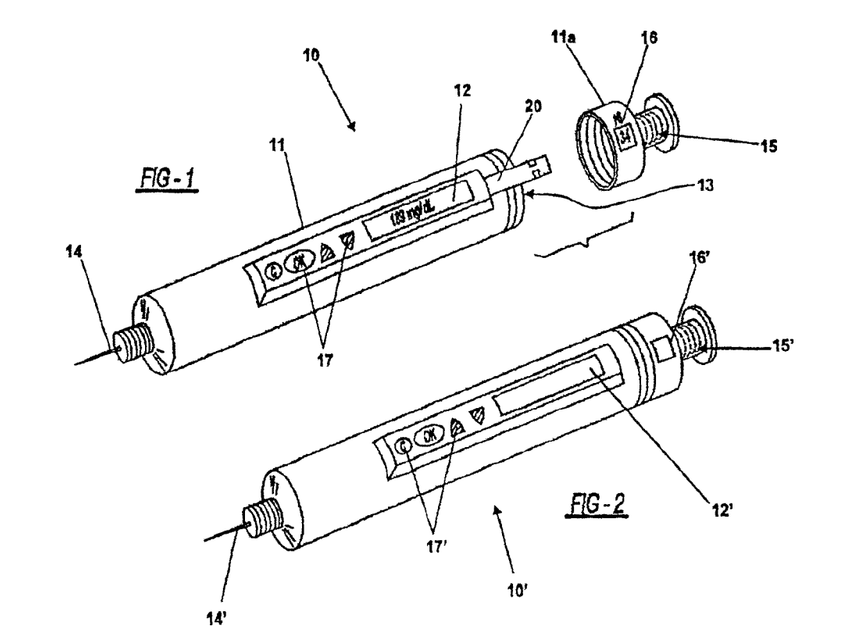
FIG. 1 is perspective view of the apparatus for diabetes management according to an exemplary embodiment.
FIG. 2 is a perspective view of the apparatus for diabetes management according to a second exemplary embodiment.

Referring now to the drawings, wherein like numerals refer to like or corresponding parts throughout the several views, the present invention is generally characterized as an apparatus 10 for diabetes management, the apparatus comprising a body 11 which houses:

(i) at least a first computer-readable memory (not shown) for storing data inputs corresponding at least to one or more components in a patient's present insulin dosage regimen and the patient's blood-glucose-level measurements determined at a plurality of times;

(ii) a processor (not shown) operatively connected to the at least first memory, the processor programmed at least to determine from the data inputs corresponding to the patient's blood-glucose-level measurements determined at a plurality of times whether and by how much to vary at least one of the one or more components of the patient's present insulin dosage regimen;

(iii) a display screen 12 operatively connected to the processor;

(iv) a quantity of insulin (not visible) disposed in an internal opening 13 in the body 11;

(v) a needle 14 communicating with the quantity of insulin for delivering insulin to the patient;

(vii) means for effecting delivery of a portion of the quantity of insulin to the patient via the needle; and (vi) metering means for controlling the portion of the quantity of insulin delivered to the patient via the needle (FIGS. 1 and 2).

The data inputs corresponding at least to one or more components in a patient's present insulin dosage regimen and the patient's blood-glucose-level measurements determined at a plurality of times stored in the at least first memory may, by way of non-limiting example, comprise those data inputs described in the inventions as set forth in US Published Applications 20090253970 and 20090253973, the disclosures of which published patent applications are incorporated herein by reference in their entireties. Relatedly, operation of the processor to at least determine from the data inputs whether and by how much to vary at least one of the one or more components of the patient's present insulin dosage regimen may, by way of non-limiting example, correspond to operation of the inventions as set out in the aforesaid US Published Applications 20090253970 and 20090253973. As explained more fully therein, the operation of the exemplary embodiments of those inventions is characterized by the determination of whether and by how much to vary one or more components of a patient's insulin dosage regimen based upon the determined efficacy of that regimen in view of blood glucose level measurements recorded as of the time of the determination. As a non-limiting example, determination of whether and by how much to vary a patient's present insulin dosage regimen is undertaken both on the basis of evaluations conducted at predefined time intervals (every 7 days, for example) as well as asynchronously to such intervals. The asynchronous determinations will evaluate the patient's blood-glucose-level data for safety each time a new blood-glucose-level measurement is received to determine whether any urgent action, including any urgent variation to the patient's present insulin dosage, is necessary. More particularly, each time a new patient blood glucose-level measurement is received into the memory it is accessed by the processor and sorted and tagged according to the time of day the measurement was received and whether or not it is associated with a certain event, e.g., pre-breakfast, bedtime, nighttime, etc. Once so sorted and tagged, the new and/or previously recorded blood-glucose-level measurements are subjected to evaluation for the need to update on the basis of the passage of a predefined period of time measured by a counter, as well as the need to update asynchronously for safety. For instance, a very low blood glucose measurement representing a severe hypoglycemic event or the accumulation of several low measurements in the past few days may lead to an update in the patient's insulin dosage regimen, while an update to that regimen may otherwise be warranted if a predefined period of time (e.g., 7 days) has elapsed since the patient's insulin dosage regimen was last updated. If an excessive number of such hypoglycemic events is not indicated, then the algorithm queries whether or not it is time to update the patient's insulin dosage regimen irrespective of the non-occurrence of hypoglycemic events, and based instead upon the passage of a predefined interval of time (e.g., 7 days) since the need to update the patient's insulin dosage regimen was last assessed. If such an update is not indicated, i.e., because an insufficient time interval has passed, then no action is taken with respect to the patient's insulin dosage and the algorithm ends until the next blood glucose-level measurement data are input.

Where, as in the embodiment of FIGS. 1 and 2, the memory and processor are housed in the body 11 of the apparatus, data entry means, such as the illustrated single or multi-function buttons or keys 17, are provided to facilitate the entry of, for example and without limitation, one or more of the data inputs corresponding at least to one or more components in a patient's present insulin dosage regimen.

Power to operate the apparatus, including the display and processor, may be provided by one or more batteries (not shown) disposed in the body 11. These one or more batteries may be rechargeable or single-use, replaceable or irreplaceable.

The means for effecting delivery of a portion of the quantity of insulin may take the form of a plunger 15 operative in known fashion to dispense a portion of insulin through the needle 14 upon actuation of the plunger. Such means are found in conventional insulin pens. Of course, any other means employed to dispense insulin in conventional insulin pens may be substituted.

In order to control the portion of the quantity of insulin delivered to the patient via the needle 14, metering means are provided. In one form, such metering means may comprise any mechanism employed in conventional insulin pens, for instance, to ensure that actuation of the plunger 15 effectuates delivery of only a defined portion of insulin. According to such construction of the apparatus, unlimited actuation of the plunger 15 dispenses a predefined portion of insulin via the needle 14. The metering means preferably, though not necessarily, include a dial or other mechanism the selective movement of which would limit actuation of the plunger 15 in predefined increments corresponding to predefined measurements of insulin. A display 16 provided on the apparatus 10 indicates the current setting of the metering means so that the patient can know how much insulin will be dispensed upon actuation of the plunger 15. Of course, such display may be provided on the display screen 12 in the alternative. Thus, by actuation of the metering means, a patient can, as desired, modify the apparatus so that actuation of the plunger will dispense a portion of the quantity of insulin corresponding to a recommended insulin dose corresponding to the processor's determination of a recommended insulin dosage regimen (which may be the patient's existing regimen or a regimen modified according to the algorithm employed by the processor).

In an alternative embodiment, the delivery means may comprise an electro-mechanical device disposed in the body 11 and operative to automatically effect delivery of a portion of the quantity of insulin via the needle 14 upon actuation of one of a plurality of single-purpose or multi-function buttons 17 provided on the apparatus. Further according to this embodiment, the metering means are likewise automatic. Once a recommended insulin dosage regimen has been determined by the processor (whether that regimen is an existing or modified regimen), the electro-mechanical device is automatically adjusted by the processor so that the subsequent actuation of the delivery means (such as, for instance, via on ore more of the buttons 17) delivers to the patient a dose of insulin corresponding to a recommended current insulin dose, determined by the processor, that may be displayed on the display screen 12.

According to a still further embodiment, the delivery means may comprise the manually actuated plunger heretofore described, while the metering means may be an electro-mechanical device the operation of which is automatically effected by the processor. In this fashion, the amount of insulin dispensed by a patient's manual actuation of the plunger would automatically correspond to the recommended current insulin dose that may be displayed on the display screen 12.

As shown in FIG. 1, the quantity of insulin may be capable of replenishment upon exhaustion. To this end, the quantity of insulin may be contained in cartridges (not depicted) that are selectively removable from the body 11 so as to be replaceable upon exhaustion of the insulin supply therein. In order to permit access to the cartridges, body 11 comprises, in the exemplary embodiment, a removable cap 11a permitting access to the internal opening 13. The cartridges may be, for instance, in the form of compressible capsules (made, for instance, of plastic) acted upon by the plunger 15 during administration of a dose of insulin. It is also contemplated that such cartridges may take any form employed in conventional insulin pens.

Alternatively, the apparatus 10' may, as shown in FIG. 2, be for "single use," meaning that the quantity of insulin contained therein would suffice for a limited number of doses and would thereafter be incapable of replenishment. For instance, it is typically the case that conventional insulin pens contain about 300 insulin units [IU]. A similar amount could, without limitation, constitute the quantity of insulin contained in the apparatus 10'. For some patients, such an amount may last for 10 or more days, while for others this can represent a daily consumption of insulin.

Needle 14 is preferably, though not necessarily, removably connected to the body 11 so as to be disposable following use and thereafter replaceable with a sanitary needle. Such removable connection, typical of conventional insulin pens, may be accomplished in any conventional fashion.

According to any of the foregoing, it is further contemplated that the apparatus 10, 10' may include means for preventing a patient from administering an injection when there is no or an insufficient amount of insulin remaining in the apparatus. Such means may take the form of a visual warning, provided for instance on the display 12, 12'. Alternatively, or in addition, the apparatus may be programmed to physically prevent operation of the delivery means. Such may comprise an electro-mechanical device (which may be the same as or separate from those described in connection with the delivery and/or metering means), the operation of which is effected by the processor, which precludes actuation of the delivery means when it is determined by the processor (for instance, by calculation from the known initial quantity of insulin provided, the number of times the delivery means are actuated, and the dose/portion of insulin delivered each time the delivery means are actuated) that an insufficient amount of insulin remains to deliver a recommended dose of insulin or another, predefined dose.

Optionally, the apparatus 10 may, as shown in FIG. 1, further comprise a test strip port of known construction housed in the body 11 for receiving a test strip 20, such that the apparatus is capable of acting also as a blood glucose meter. To this end, the processor is operative to determine a patient's current blood glucose level measurement from a sample of the patient's blood provided on a test strip 20. Per this embodiment, display 12 may, optionally, provide a visual indication of the patient's current blood-glucose-level reading (e.g., "189 mg/dL" as shown in FIG. 1). According to this embodiment, the blood-glucose-level readings so determined comprise data inputs stored in the at least one memory and employed by the processor at least to determine whether and by how much to vary at least one of the one or more components of the patient's present insulin dosage regimen (such as, for instance, according to the manner of operation of the inventions as disclosed in the aforesaid US Published Applications 20090253970 and 20090253973).

Display screen 12 may, by way of non-limiting example, comprise an LCD screen, the apparatus being programmed, according to convention, to display thereon such information displays as described herein (e.g., a recommended insulin dose corresponding to the processor-determined insulin dosage regimen). Where the apparatus 10 is operative to determine blood glucose level measurements, and further includes data entry means such as the buttons 17 herein described to permit the patient and/or other user's to input data corresponding at least to one or more components in a patient's present insulin dosage regimen and data inputs related to the patient's blood glucose measurements, the display screen 12 may be operative so as to display information displays corresponding to at least the following:

a patient's current blood glucose level measurement;

an event associated with the said current blood glucose level measurement;

a measurement for the number of carbohydrates associated with the said event; and a recommended insulin dose corresponding to the processor-determined insulin dosage regimen.

Optionally, the display screen 12 may further be operative to successively display a summary screen displaying simultaneously information corresponding to that provided on each of two or more of the foregoing information displays, including: a patient's current blood glucose level measurement, an event associated with the said current blood glucose level measurement, a measurement for the number of carbohydrates associated with the said event, and the recommended insulin dose.

According to the foregoing embodiment of the invention, the patient and/or other user is able to enter, in addition to, for instance, such other data as corresponds to one or more components in a patient's present insulin dosage regimen, data related to a particular blood glucose level measurement as determined by the processor from a sample of the patient's blood. These data include, for instance and without limitation, an appropriate event (e.g., breakfast, lunch, dinner) associated with a current blood glucose measurement as displayed on display 12, as well as the number of carbohydrates associated with the event.

Optionally, the apparatus 10 is programmed to enable a patient and/or other user to selectively override, such as by using one or more of the plurality of buttons 17, a recommended current insulin dose displayed on the display screen 12. To the extent that the metering means are automatically adjusted to effect delivery of the recommended insulin dose, it is contemplated that the metering means would be further adjusted in response to any change in the recommended current insulin dose made by the patient and/or other user.

Figure 3:
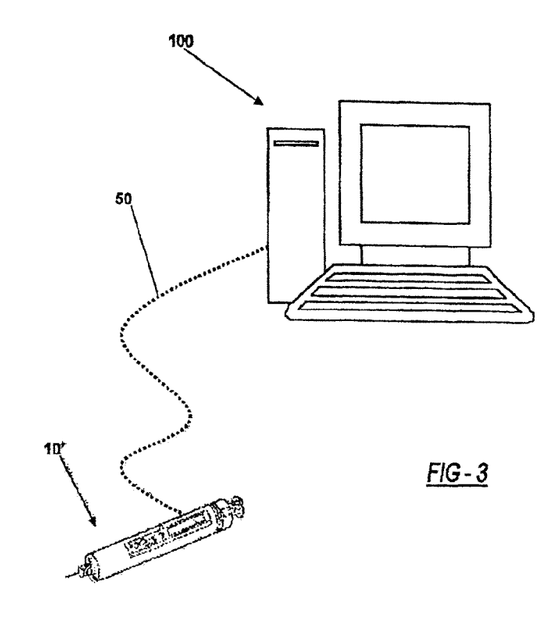
FIG. 3 is a diagrammatic depiction of the inventive system according to a first exemplary embodiment thereof.

Referring next to FIG. 3, it is further contemplated that the apparatus 10' be capable (particularly, though not exclusively, where fashioned for single use) of communicating remotely (shown by the dashed line 50) with a device 100, such as a general-purpose computer (shown), cell phone, IPHONE, IPOD, PDA, etc., to which patient data, such as, for instance, blood-glucose-level data, may be transferred and stored for later use. Such remote communication may be accomplished via a communication cable, for instance a USB cable, connectable to the apparatus and the remotely positioned device. Alternatively, such remote communication may be accomplished wirelessly, such as, for instance, via any conventional wireless transmission protocol.

In similar fashion, it is further contemplated that the apparatus of the present invention (especially, although again not exclusively, where fashioned for single-use) include means to communicate with like apparatus via a communication cable, wirelessly, or any other conventional communication means. This may be necessary, for instance, to transfer the patient's present insulin dosage regimen data, as well as historical blood-glucose-level measurement data from the apparatus 10' the insulin supply of which is exhausted to a second, unspent apparatus. It will be appreciated that while such utility may be particularly desired where the apparatus 10' is of "single-use" design, it may also be desired in order to transfer such data as is stored in a first apparatus to a second, like apparatus upon, or prior to, failure of the first.

Figure 4:
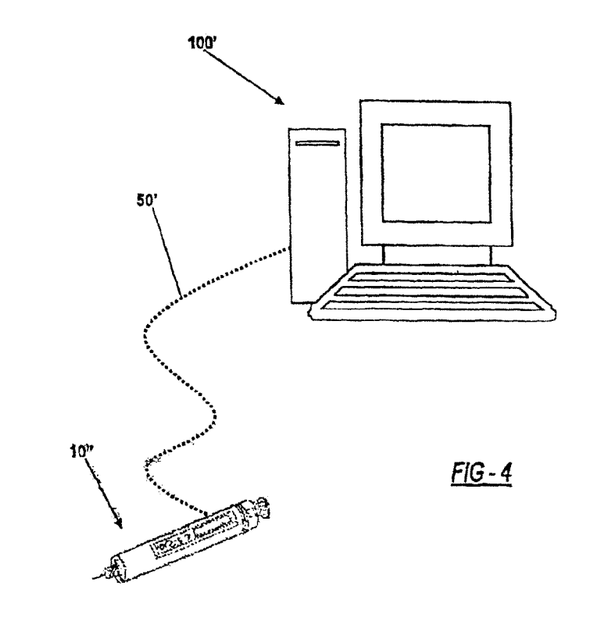
FIG. 4 is a diagrammatic depiction of the inventive system according to a second exemplary embodiment thereof.

Referring next to FIG. 4, there is depicted an alternative embodiment of the apparatus 10" according to which a memory for storing data inputs corresponding at least to one or more components in a patient's present insulin dosage regimen and/or the patient's blood-glucose-level measurements determined at a plurality of times, as well as a processor operatively connected to memory and programmed at least to determine from the data inputs corresponding to the patient's blood-glucose-level measurements determined at a plurality of times whether and by how much to vary at least one of the one or more components of the patient's present insulin dosage regimen, are disposed in a device 100' remote from the apparatus 10". Device 100', which may be a general-purpose computer (as depicted), cell phone, IPHONE, IPOD, PDA or a purpose-built unit, is adapted to communicate remotely (shown by dashed lines 50') with the apparatus 10" so that data may be transferred between the device 100' and the apparatus 10" (which includes a processor and at least a first memory for storing such data but which is not, as indicated, itself operative to determine from the data inputs corresponding to the patient's blood-glucose-level measurements determined at a plurality of times whether and by how much to vary at least one of the one or more components of the patient's present insulin dosage regimen). Such remote communication may be accomplished via a communication cable, for instance a USB cable, connectable to the apparatus 10" and the remotely positioned device 100'. Alternatively, such communication may be accomplished wirelessly, such as, for instance, via any conventional wireless transmission protocol.

According to this embodiment, data corresponding to the patient's insulin dosage regimen and the patient's blood-glucose-level measurements are stored in the memory of the device 100', the processor of which is operative to access these data and determine at least whether and by how much to vary at least one of the one or more components of the patient's present insulin dosage regimen. Upon completion of this determination, information corresponding to at least a recommended current insulin dose may be transferred to the apparatus 10" to be displayed on display 12 to be acted upon in any manner as heretofore described.

Per this embodiment of the invention, the data corresponding to the patient's insulin dosage regimen may be input on one or more occasions by the patient's physician or other healthcare professional. The patient's blood-glucose-level measurements may be transferred to the memory of the device 100' via a separate blood glucose meter or, to the extent that such functionality is provided in the apparatus 10" according to the embodiment as described herein, may be provided directly from the apparatus 10".

Figure 5:
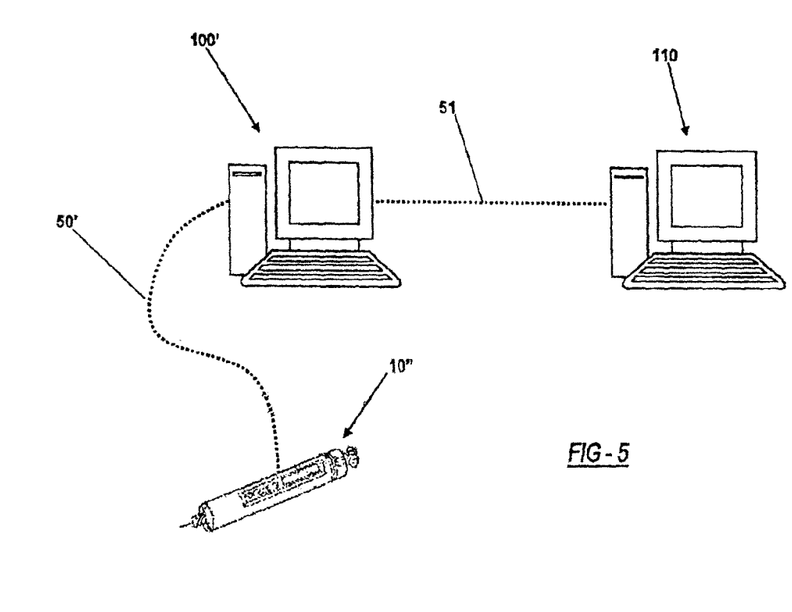
FIG. 5 is a diagrammatic depiction of the inventive system according to a third exemplary embodiment thereof.

Referring next to FIG. 5, it is further contemplated that the embodiment of FIG. 4 may be augmented by the provision of one or more additional devices 110 in communication (shown by dashed line 51, which represents either a wireless or wired connection) with the device 100' to facilitate remote entry of data, such as, for instance, data corresponding to the patient's insulin dosage regimen. Per this embodiment of the invention, data corresponding to the patient's insulin dosage regimen may be input on one or more occasions by the patient's physician or other healthcare professional via the device 110 and these data thereafter transferred, such as, for instance and without limitation, via the internet, to the memory of the device 100'.

The foregoing description of the exemplary embodiment of the invention has been presented for purposes of illustration and description. It is not intended to be exhaustive of, or to limit, the invention to the precise form disclosed, and modification and variations are possible in light of the above teachings or may be acquired from practice of the invention. The embodiment shown and described in order to explain the principles of the invention and its practical application to enable one skilled in the art to utilize the invention in various embodiments and with various modifications as are suited to the particular application contemplated. Accordingly, all such modifications and embodiments are intended to be included within the scope of the invention. Other substitutions, modifications, changes and omissions may be made in the design, operating conditions, and arrangement of the exemplary embodiments without departing from the spirit of the present invention.

The invention in which an exclusive property or privilege is claimed is defined as follows:

1. An apparatus comprising:
    a body housing;
    at least a first memory for storing data inputs corresponding at least to one or more components in a patient's present insulin dosage regimen and a patient's blood-glucose-level measurements determined at a plurality of times;
    a processor operatively connected to the at least first memory, the processor programmed at least to determine from the data inputs corresponding to the patient's blood-glucose-level measurements determined at a plurality of times within a predetermined time interval whether and by how much to vary at least one of the one or more components of the patient's present insulin dosage regimen,
        wherein the predetermined time interval is longer than a time period between any two consecutive blood-glucose-level measurements, and
        wherein said determination occurs only after a passage of the predetermined time interval since the need to update the patient's insulin dosage regimen was last assessed or if the most recent blood-glucose measurement is a severe hypoglycemic event or a predetermined plurality of hypoglycemic measurements have been recorded during an elapsed portion of the predetermined time interval, and
    a display screen operatively connected to the processor;
    a cartridge for the storage of a quantity of insulin;
    a needle communicating with the cartridge for the storage of the quantity of insulin for delivering insulin to the patient;
    a delivery mechanism for effecting the delivery of an amount of insulin to the patient via the needle; and
    a meter for controlling the amount of insulin delivered to the patient via the needle.

2. The apparatus of claim 1, wherein the cartridge is selectively removable from the body housing so as to be replaceable upon exhaustion of the quantity of insulin therein.

3. The apparatus of claim 1, wherein the quantity of insulin cannot be replenished upon exhaustion thereof.

4. The apparatus of claim 1, wherein the body housing further houses a test strip port for receiving a test strip, and the processor is operative to determine a patient's current blood glucose level measurement from a sample of the patient's blood provided on a test strip.

5. The apparatus of claim 1, wherein the display screen is further operative to display a patient's current blood glucose level measurement.

6. The apparatus of claim 1, further comprising a transceiver for communicating data from the first memory to a remote device for remote storage.

7. The apparatus of claim 1, further comprising a transceiver for communicating data from the first memory to a second apparatus for taking blood glucose measurements and optimizing a patient's insulin dosage regimen over time.

8. The apparatus of claim 1, further comprising a mechanism for preventing a patient from administering an injection when there is an insufficient quantity of insulin remaining in the apparatus.

* * * * *